(12) United States Patent  
Jeanne et al.

(10) Patent No.: US 12,251,192 B2  
(45) Date of Patent: Mar. 18, 2025

(54) METHOD AND SYSTEM TO MEASURE LOCALIZED INFLAMMATION USING AN ORAL CARE DEVICE

(71) Applicant: KONINKLIJKE PHILIPS N.V., Eindhoven (NL)

(72) Inventors: Vincent Jeanne, Migne Auxances (FR); Yekaterina Aleksandrovna Borisenko, Lynnwood, WA (US); Steven Charles Deane, Cambridge (GB); Olaf Thomas Johan Antonie Vermeulen, Oss (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 677 days.

(21) Appl. No.: 16/495,527

(22) PCT Filed: Mar. 20, 2018

(86) PCT No.: PCT/EP2018/056971  
§ 371 (c)(1),  
(2) Date: Sep. 19, 2019

(87) PCT Pub. No.: WO2018/172330  
PCT Pub. Date: Sep. 27, 2018

(65) Prior Publication Data  
US 2020/0022583 A1    Jan. 23, 2020

Related U.S. Application Data

(60) Provisional application No. 62/473,626, filed on Mar. 20, 2017.

(30) Foreign Application Priority Data

May 5, 2017 (EP) ..................................... 17169756

(51) Int. Cl.  
*A61B 5/00* (2006.01)

(52) U.S. Cl.  
CPC .... *A61B 5/0088* (2013.01); *A61B 2560/0425* (2013.01)

(58) Field of Classification Search  
CPC ...................... A61B 5/0088; A61B 2560/0425  
(Continued)

(56) References Cited

U.S. PATENT DOCUMENTS 8,054,463 B2    11/2011  Morris  
8,073,212 B2 *  12/2011  Gerlach ............... A61B 5/0088  
                                                            382/128

(Continued)

FOREIGN PATENT DOCUMENTS

JP      2007151782 A      6/2007  
JP       200829267 A  *   7/2008

OTHER PUBLICATIONS

PCT/EP2018/056971 ISR & Written Opinion, Sep. 4, 2018, 18 Page Document.

*Primary Examiner* — Sunghyoun Park

(57) ABSTRACT

A method (700) for localizing inflammation within a user's mouth using an oral care device (10), comprising the steps of: (i) emitting (720) light by one or more light emitters (42) of the oral care device; (ii) detecting (730), by a light detector (40) of the oral care device, reflectance from a surface at each of a plurality of locations within the user's mouth to generate reflectance data for each of the plurality of locations; (iii) determining (750), by the controller, for the plurality of locations, whether gingiva at that location is inflamed; and (iv) providing (760), via a user interface (46) of the oral care device, information to the user regarding the inflamed location or locations.

14 Claims, 9 Drawing Sheets

(58) Field of Classification Search
USPC ......... 600/589, 587, 590; 386/210, 223, 224
See application file for complete search history.

(56) References Cited

U.S. PATENT DOCUMENTS

| | | | |
|---|---|---|---|
| 8,721,327 B2 | 5/2014 | Karazivan et al. | |
| 9,814,522 B2 | 11/2017 | Spruit | |
| 2007/0036430 A1 | 2/2007 | Katsumata | |
| 2008/0026340 A1 | 1/2008 | Gerlach et al. | |
| 2013/0323673 A1 | 12/2013 | Karazivan et al. | |
| 2014/0037180 A1 | 2/2014 | Wang et al. | |
| 2014/0177931 A1 | 6/2014 | Kocherscheidt et al. | |
| 2014/0313299 A1 | 10/2014 | Gebhardt et al. | |
| 2015/0297085 A1 | 10/2015 | Simons et al. | |
| 2016/0015493 A1* | 1/2016 | Ertl ....................... | A61B 6/512 |
| 2016/0038076 A1 | 2/2016 | Muller et al. | |
| 2016/0270716 A1 | 9/2016 | Guan et al. | |
| 2017/0215997 A1* | 8/2017 | Martin .................... | A61B 6/14 |

\* cited by examiner

METHOD AND SYSTEM TO MEASURE LOCALIZED INFLAMMATION USING AN ORAL CARE DEVICE

CROSS-REFERENCE TO PRIOR APPLICATIONS

This application is the U.S. National Phase application under 35 U.S.C. § 371 of International Application No. PCT/EP2018/056971, filed on Mar. 20, 2018, which claims the benefit of U.S. Provisional Patent Application No. 62/473,626, filed on Mar. 20, 2017 and European Patent Application No. 17169756.8, filed on May 5, 2017. These applications are hereby incorporated by reference herein.

FIELD OF THE INVENTION

The present disclosure is directed generally to methods and systems for detecting localized gingival inflammation using an oral care device.

BACKGROUND

Proper tooth brushing, including length and coverage of brushing, helps promote long-term dental health. Many dental problems are experienced by individuals who either do not regularly brush their teeth or who do so inadequately, especially in a particular area or region of the oral cavity. Among individuals who do brush regularly, improper brushing habits can result in poor coverage of brushing and thus surfaces that are not adequately cleaned during a cleaning session, even when a standard brushing regimen, such as brushing for two minutes twice daily, is followed.

Indeed, it is estimated that 50% of the adult population in the United States is affected by periodontal disease, with severity of disease ranging from gingivitis to periodontitis. However, consumers are often not able to detect early signs of periodontal disease. Accordingly, such diseases may only be detected during dental visits when the disease is already advanced and significantly harder to treat.

Inflammation of tissues within the mouth is one of the key signs of periodontal disease. Detecting inflammation would signal the existence of a disease state, and would alert the individual to the need for treatment by a professional. However, existing methods and devices are unable to adequately identify or quantify inflammation of tissues, particularly localized inflammation. For example, handheld devices enable poor detection of gingival inflammation, as these devices either analyze large areas of the mouth resulting in a large signal-to-noise ratio that interferes with detection, or require so many measurements that they are not user friendly. As a result, periodontal disease is often not detected.

Accordingly, there is a continued need in the art for user-friendly oral care methods and devices that maximize signal-to-noise ratio and enhance detection of localized gingival inflammation.

SUMMARY OF THE INVENTION

The present disclosure is directed to inventive methods and systems for detecting tissue inflammation using an oral care device. Various embodiments and implementations herein are directed to an oral care device configured to obtain measurements of gingival tissue to identify localized gingival inflammation. The oral care device comprises a specialized sensor with a unique configuration of one or more light emitters and one or more photodetectors or imagers to obtain information about gingival tissue. The oral care device also comprises a signal analysis module that analyzes the obtained information about the gingival tissue and identifies locations that are likely inflamed. According to an embodiment, the oral care device alerts the user in real-time or via a post-cleaning report to the existence of inflammation, and can optionally provide localization information to the user.

Generally in one aspect, a method for localizing gingival inflammation within a user's mouth using an oral care device is provided. The method includes the steps of: (i) emitting light by one or more light emitters of the oral care device; (ii) detecting, by a light detector of the oral care device, reflectance from a surface at each of a plurality of locations within the user's mouth to generate reflectance data for each of the plurality of locations; (iii) determining, by the controller, whether gingiva at that location is inflamed; and (iv) providing, via a user interface of the oral care device, information to the user regarding the inflamed location or locations.

According to an embodiment, the one or more light emitters and the light detector are positioned such that the surface at each of the plurality of locations is not directly illuminated by the one or more light emitters.

According to an embodiment, the method further includes the step of detecting a proximity to the gingiva.

According to an embodiment, the method further includes the step of communicating information regarding the inflamed location or locations to a remote third party.

According to an embodiment, the method further includes the step of determining which of the plurality of locations comprises gingiva.

According to an embodiment, the step of determining which of the plurality of locations comprise gingiva comprises discarding reflectance data for locations determined not to comprise gingiva. According to an embodiment, the step of discarding reflectance data for locations determined not to comprise gingiva comprises the steps of: (i) generating a reflectance ratio for each of the plurality of locations, wherein the reflectance ratio comprises a measured value for a first wavelength of the reflectance data over a measured value for a second wavelength of the reflectance data; (ii) comparing the generated reflectance ratio to a predetermined threshold; and (iii) discarding reflectance data for each of the plurality of locations for which the generated reflectance ratio falls below the predetermined threshold.

According to an embodiment, the step of determining which of the plurality of locations comprise gingiva comprises weighting the generating reflectance data for at least some of the plurality of locations.

According to an embodiment, the step of determining whether gingiva at a location is inflamed comprises determining an approximate tissue oxygenation level of the gingiva at each of the remaining plurality of locations, wherein a low tissue oxygenation level indicates gingiva inflammation.

According to an embodiment, the user interface provides information about which of the plurality of locations within the user's mouth are inflamed. According to an embodiment, the user interface provides information about an inflammation level of at least one of the plurality of locations within the user's mouth.

According to an embodiment, the oral care device comprises a single light emitter and a plurality of light detectors.

According to an embodiment, the oral care device comprises a single light detector and a plurality of light emitters.

According to an aspect, a device configured to localize gingival inflammation within a user's mouth is provided. The device includes: one or more light emitters configured to emit light at a plurality of locations within the user's mouth; one or more light detectors configured to generate reflectance data from a surface at each of the plurality of locations; a controller configured to determine, for the plurality of locations, whether gingiva at that location is inflamed; and a user interface configured to provide information to the user regarding the inflamed location or locations.

According to an aspect, an inflammation localization system configured to localize gingival inflammation within a user's mouth is provided. The system includes: one or more light emitters each comprising one or more light sources configured to emit light within the user's mouth; one or more light detectors configured to generate reflectance data from a surface at each of a plurality of locations within the user's mouth; a controller comprising an inflammation detection and localization module configured to: determine, for the plurality of locations, whether gingiva at that location is inflamed; and a user interface configured to provide information to the user regarding the inflamed location or locations.

As used herein for purposes of the present disclosure, the term "controller" is used generally to describe various apparatus relating to the operation of an oral care apparatus, system, or method. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a method and device for detecting gingival inflammation using an oral care device. More generally, Applicant has recognized and appreciated that it would be beneficial to provide a system to detect localized tissue inflammation. Accordingly, the methods described or otherwise envisioned herein provide a device such as an oral care device configured to obtain measurements of gingival tissue. The oral care device comprises one or more of a variety of specialized sensor arrays having at least one light emitter and at least one photodetector or imager. Based on the sensor data, the oral care device can determine whether the analyzed tissue is inflamed, and can localize that inflammation. The oral care device can then report that information to the user or a third party.

The embodiments and implementations disclosed or otherwise envisioned herein can be utilized with any oral device, including but not limited to a toothbrush, a flossing device, an oral irrigator, or any other oral device, including a specialized handheld oral inflammation detection device.

Figure 1:
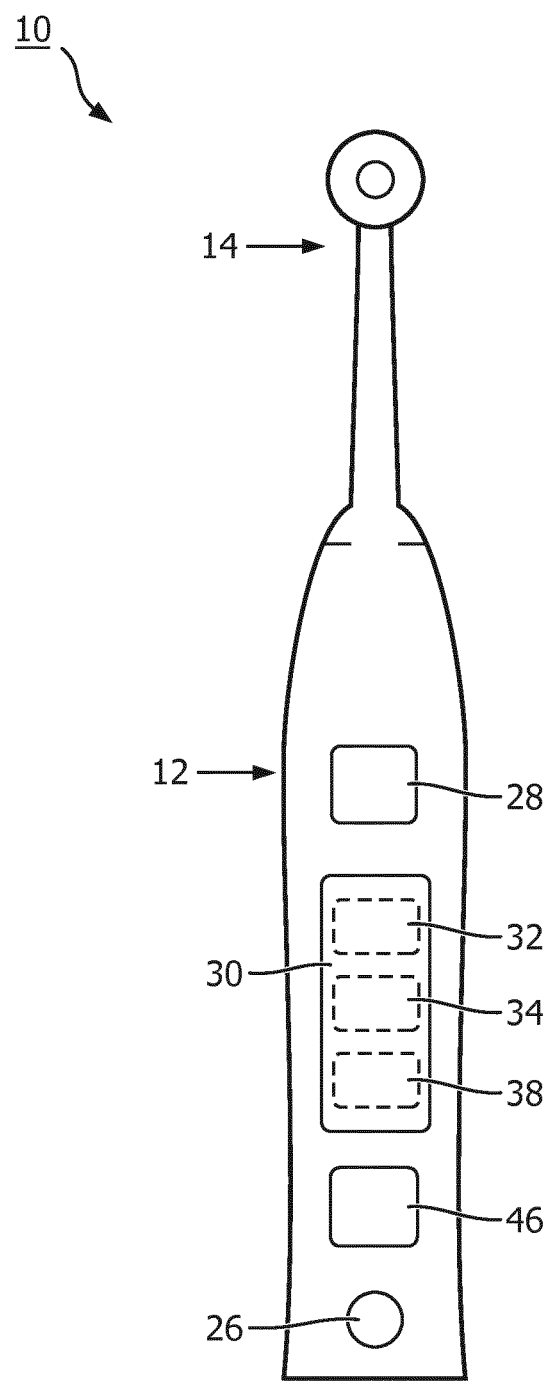
FIG. 1 is a schematic representation of an oral care device, in accordance with an embodiment.

Referring to FIG. 1, in one embodiment, is an oral care device 10 with a body portion 12 and a head member 14 mounted on the body portion. Head member 14 is can be detachably mounted onto body portion 12 such that it can periodically be replaced with a new one when a component of the device is worn out or otherwise requires replacement.

Body portion 12 is further provided with a user input 26. The user input 26 allows a user to operate the oral care device 10, for example to turn the oral care device on and off. The user input 26 may, for example, be a button, touch screen, or switch.

Oral care device 10 optionally includes one or more sensors 28. Sensor 28 is shown in FIG. 1 within body portion 12, but may be located anywhere within the device. Sensor 28 can comprise, for example, a 6-axis or a 9-axis spatial sensor system, and can include one or more of an accelerometer, a gyroscope, and/or a magnetometer to provide readings relative to axes of motion of the oral care device, and to characterize the orientation and displacement of the device. For example, the sensor 28 can be configured to provide readings of six axes of relative motion (three axes translation and three axes rotation), using for example a 3-axis gyroscope and a 3-axis accelerometer. Many other configurations are possible. Other sensors may be utilized either alone or in conjunction with these sensors, including but not limited to a pressure sensor (e.g. Hall effect sensor) and other types of sensors, such as a sensor measuring electromagnetic waveforms on a predefined range of wavelengths, a capacitive sensor, a camera, a photocell, a visible light sensor, a near-infrared sensor, a radio wave sensor, and/or one or more other types of sensors. Many different types of sensors could be utilized, as described or otherwise envisioned herein. According to an embodiment, these additional sensors provide complementary information about the position of the device with respect to a user's body part, a fixed point, and/or one or more other positions. According to an embodiment, sensor 28 is disposed in a predefined position and orientation in the oral care device 10, and the head is in a fixed spatial relative arrangement to sensor 28. Therefore, the orientation and position of the head can be easily determined based on the known orientation and position of the sensor 28.

According to an embodiment, sensor 28 is configured to generate information indicative of the acceleration and angular orientation of the oral care device 10. For example, the sensor system may comprise two or more sensors 28 that function together as a 6-axis or a 9-axis spatial sensor system. According to another embodiment, an integrated 9-axis spatial sensor can provide space savings in an oral care device 10.

The information generated by the first sensor 28 is provided to a controller 30. Controller 30 may be formed of one or multiple modules, and is configured to operate the oral care device 10 in response to an input, such as input obtained via user input 26. According to an embodiment, the sensor 28 is integral to the controller 30. Controller 30 can comprise, for example, at least a processor 32, a memory 34, and a connectivity module 38. The processor 32 may take any suitable form, including but not limited to a microcontroller, multiple microcontrollers, circuitry, a single processor, or plural processors. The memory 34 can take any suitable form, including a non-volatile memory and/or RAM. The non-volatile memory may include read only memory (ROM), a hard disk drive (HDD), or a solid state drive (SSD). The memory can store, among other things, an operating system. The RAM is used by the processor for the temporary storage of data. According to an embodiment, an operating system may contain code which, when executed by controller 30, controls operation of the hardware components of oral care device 10. According to an embodiment, connectivity module 38 transmits collected sensor data, and can be any module, device, or means capable of transmitting a wired or wireless signal, including but not limited to a Wi-Fi, Bluetooth, near field communication, and/or cellular module.

According to an embodiment, oral care device 10 can include a user interface 46 configured to provide information to a user before, during, and/or after an oral care session. The user interface 46 can take many different forms, but is configured to provide information to a user. For example, the information can be read, viewed, heard, felt, and/or otherwise interpreted concerning inflammation of one or more tissues within the mouth. According to an embodiment, the user interface 46 provides feedback to the user that includes information about where tissues are inflamed, and/or how much inflammation is present. Accordingly, the user interface may be a display that provides information to the user, a haptic mechanism that provides haptic feedback to the user, a speaker to provide sounds or words to the user, or any of a variety of other user interface mechanisms.

Figure 2:
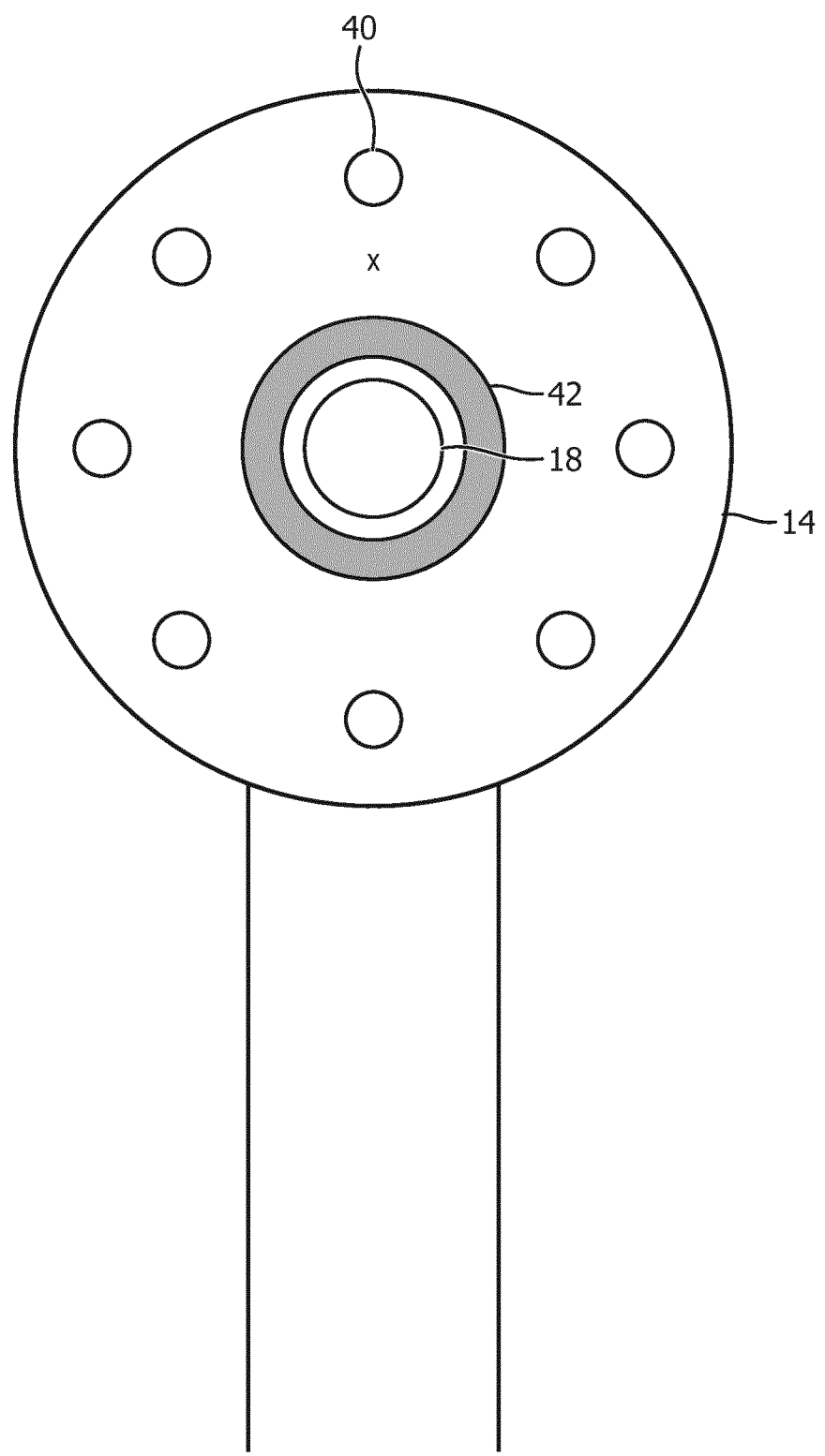
FIG. 2 is a schematic representation of a head of an oral care device, in accordance with an embodiment.

Referring to FIG. 2, in one embodiment, is a head 14 of an oral care device. According to one embodiment, the head comprises at least one light emitter 42 and at least one light receiver 40.

According to the embodiment depicted in FIG. 2, the light emitter 42 is a ring-shaped bundle of light-emitting fibers or a light-emitting light guide. The light emitter 42 is any light source, such as an LED light source, that emits light capable of facilitating the detection of gingival inflammation. According to an embodiment, the light emitters comprise combined light from a plurality of LEDs, and are connected by a light fiber or light guide from the LEDs to the light emitter on the surface of the oral care device. According to an embodiment the light source generates light in at least two wavelengths, such as 480 nm and 680 nm that allows for the characterization of oxygen saturation in human tissue, and hence the detection of localized inflammation. Generally, tissue exhibiting low tissue oxygenation indicates gingival inflammation.

Similarly, the one or more light receivers 40 are any light receivers capable of facilitating the detection of gingival inflammation. For example, according to an embodiment the light receivers are a photodetector or photodiode, or any other sensor capable of detecting light emitted by the light emitter 42. According to an embodiment, the light receivers are photodiodes connected to light fibers or light guides. Each light receiver may be configured to detect two or more wavelengths, or alternatively each light receiver may be configured to detect only a single wavelength. According to another embodiment, light receiver 40 is a pixel array configured to obtain one or more images of the tissue illuminated by the light emitted from the light emitter 42. The light receiver may comprise a plurality of detection fibers that are used simultaneously or may be time-multiplexed.

One advantage of the design of the oral care device in FIG. 2 is that the sensors are able to capture spatial information as well as gingival inflammation information. Since the information associated with each emitter-receiver couple comes from a unique tissue location, the localization of the inflammation is known.

In this embodiment, the head member 14 includes an optional guidance tip 18, which provides a tactile feedback to the user, to facilitate proper interdental positioning near the gums. According to an embodiment, when properly positioned in the mouth, each light receiver 40 measures a different part of the tissue surface, which is approximately the location between the light emitter and the light receiver. For example, when placed on the junction between two teeth and the gingiva the light emitter will illuminate the whole area, and several light receivers 40 will be on the gingiva to detect inflammation, while others will be simultaneously placed on the teeth which can be easily distinguished from the measured spectral response.

According to an embodiment, many different configurations of light emitters 42 and light detectors 40 are possible. For example, one possible configuration is a ring of three to twelve light detectors around a single light emitter, with six to eight possibly being optimal depending on the size of the head of the oral care device. Alternatively, the device may comprise a ring of three to twelve light emitters around a single light detector. Many other configurations are possible.

The one or more light emitters 42 and light detectors 40 are positioned on device 10 such that the surfaces of the gingival tissue from which data is obtained are not directly illuminated by the light emitter. For example, referring to FIG. 2, the light emitter 42 emits light into the tissue in front of it, and light detector 40 obtains reflectance data from the tissue located at or very near the "X" shown on the device in FIG. 2, although the light detector could also obtain reflectance data from the tissue located in front of it as well. According to an embodiment, therefore, the light emitters and the surfaces from which data is obtained are not overlapping. This is in contrast to a camera system in which imaged surfaces are directly illuminated. When a surface is directly illuminated, for example, detection or an image is dominated by near-surface scattering, which prevents the analysis of the gingival tissue as described herein.

Figure 3:
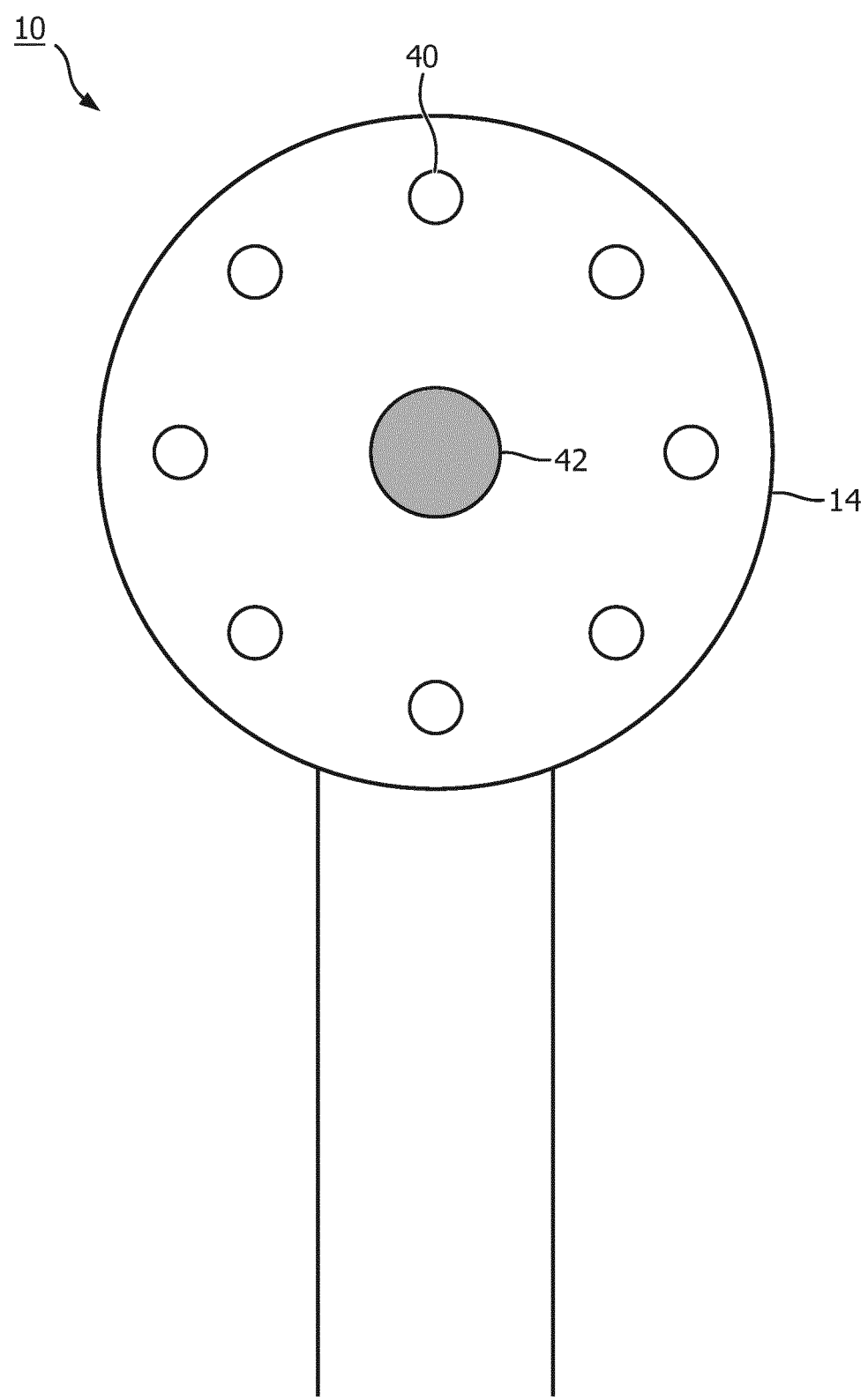
FIG. 3 is a schematic representation of a head of an oral care device, in accordance with an embodiment.

For example, referring to FIG. 3 is an embodiment of an oral care device 10 configured primarily to measure gingival inflammation. The oral care device comprises a head member 14 having a single centralized light emitter 42 and a plurality of light detectors 40. According to a similar embodiment, the device may comprise a single centralized light detector 40 and a plurality of light emitters 42.

Figure 4:
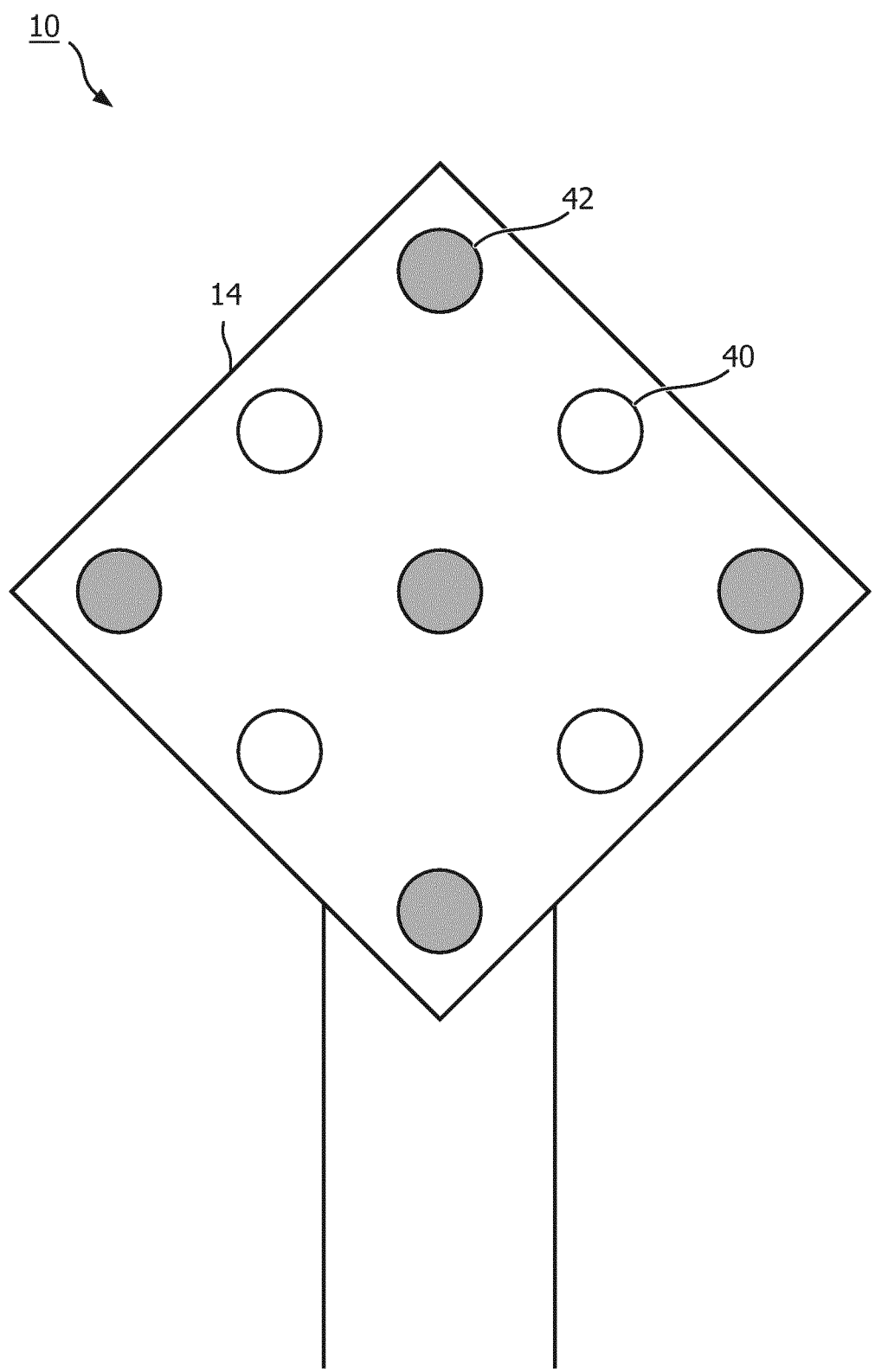
FIG. 4 is a schematic representation of a head of an oral care device, in accordance with an embodiment.

Referring to FIG. 4 is another embodiment of an oral care device 10 configured to measure gingival inflammation. The oral care device comprises a head member 14 having five light emitters 42 and four light detectors 40. The head of the oral care device is roughly diamond shaped, although many other shapes and sizes are possible. By exciting different light emitters and analyzing the signal detected at each light detector, different areas of the gingiva underneath are sensed. Time multiplexing may be performed by sequential illumination with light. Additionally, the detection sources may also be multiplexed. However, it is not necessary that both the light emitters and the light detectors be multiplexed. For example, if the light emitters can be illuminated separately, all the light detectors can share a single detector module or mechanism without reducing spatial resolution. The configuration shown in FIG. 3 may provide good access to the interdental region where gingivitis is common.

Figure 5:
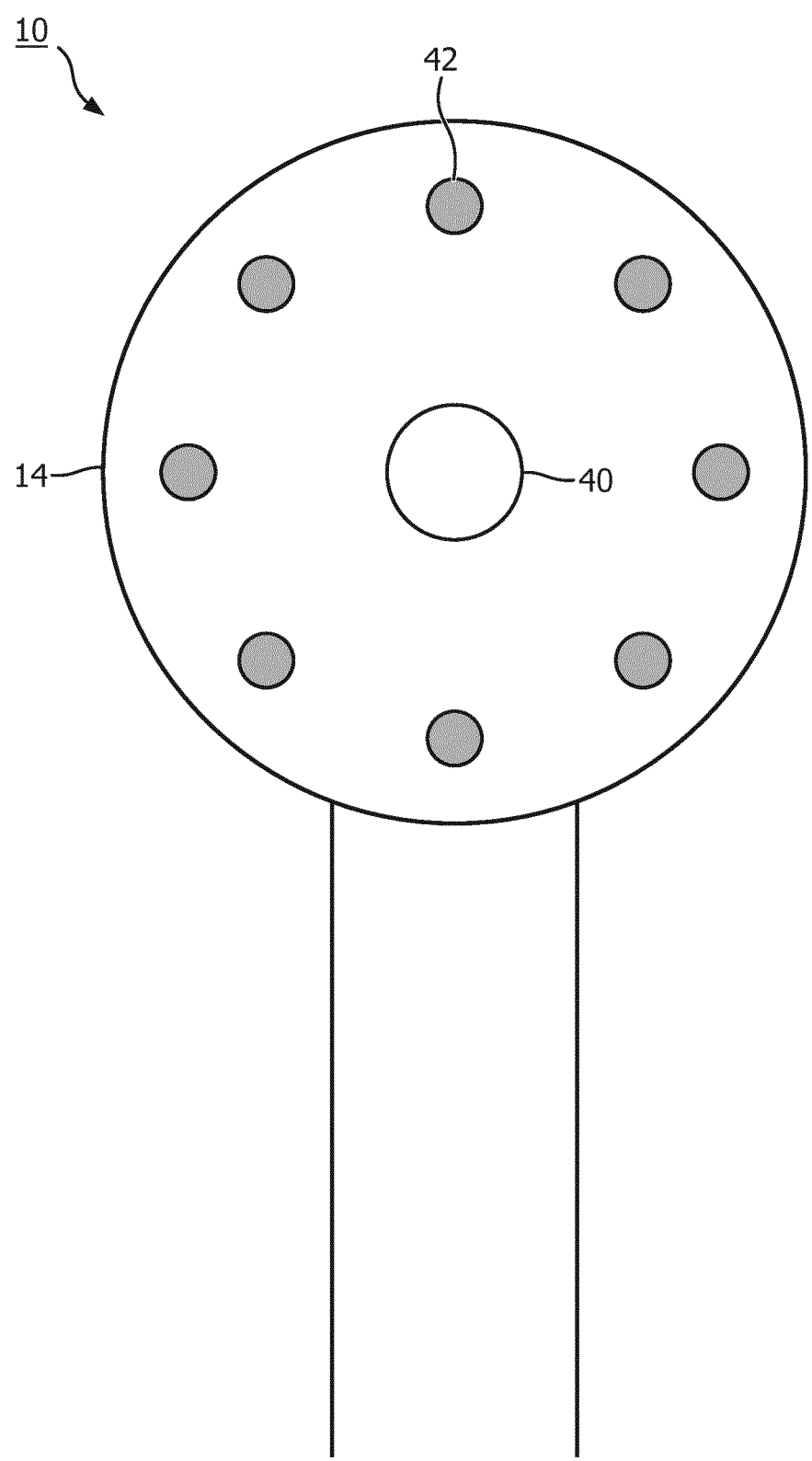
FIG. 5 is a schematic representation of a head of an oral care device, in accordance with an embodiment.

Referring to FIG. 5 is another embodiment of an oral care device 10 configured to measure gingival inflammation. The oral care device comprises a head member 14 having a single centralized light detector 40 and a plurality of light emitters 42. According to this embodiment, the single centralized light detector 40 is a microspectrometer.

Figure 6:
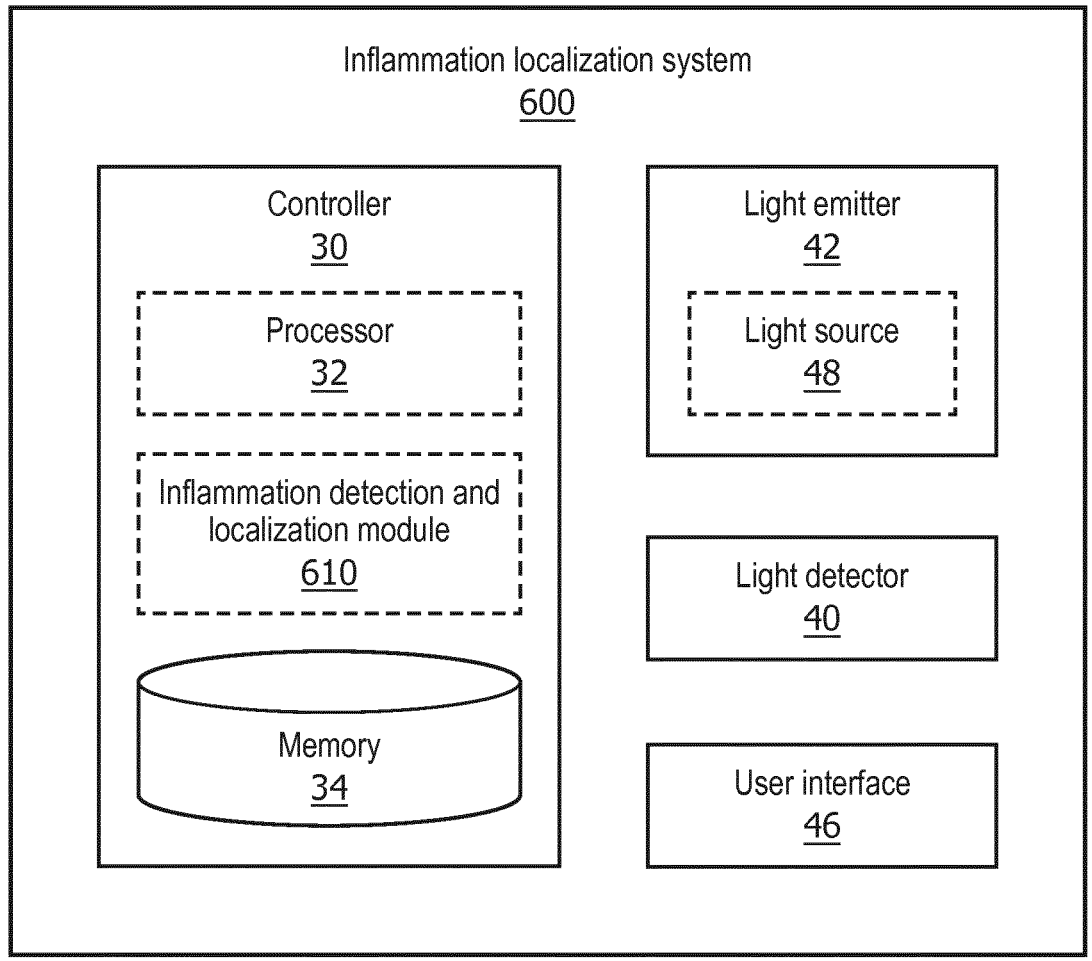
FIG. 6 is a schematic representation of an inflammation localization system, in accordance with an embodiment.

Referring to FIG. 6, in one embodiment, is an inflammation localization system 600. According to an embodiment, inflammation localization system 600 includes a controller 30 comprising a processor 32 and a memory 34. The inflammation localization system also comprises one or more light emitters 42 with one or more light sources 48. Inflammation localization system 600 includes one or more light detectors 40 which provide sensor data to the controller 30. Controller 30 of inflammation localization system 600 includes an inflammation detection and localization module 610. The inflammation detection and localization module analyzes sensor data from the one or more light detectors 40, and optionally device localization information from sensor 28, and determines whether the analyzed tissue is inflamed and where that tissue is located. The inflammation localization system also includes a user interface 46, which provides information to the user about the status and/or location of the tissue. User interface 46 can be or can comprise a feedback module that provides direct feedback to the user via a haptic signal, audio signal, visual signal, and/or any other type of signal.

According to an embodiment, inflammation localization system 600 can be implemented as a flosser, as shown in FIG. 1. According to another embodiment, inflammation localization system 600 can be implemented as any device configured to come into proximity with tissues that can be quantified. For example, inflammation localization system 600 can be implemented as another oral care device such as a toothbrush, an oral irrigator, a tongue cleaner, or any other oral care device.

Figure 7:
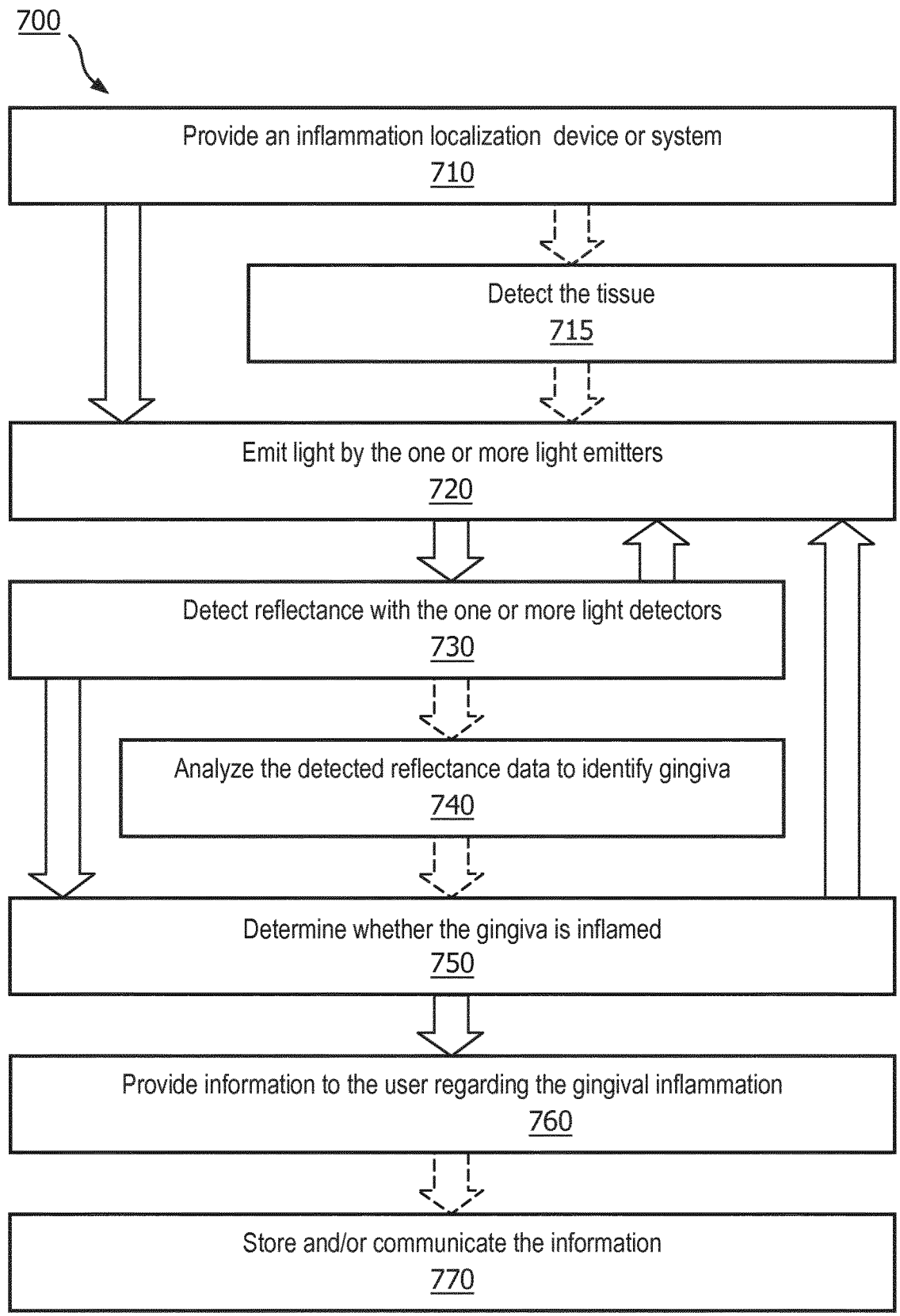
FIG. 7 is a flowchart of a method for localizing gingiva inflammation, in accordance with an embodiment.

Referring to FIG. 7, in one embodiment, is a flowchart of a method 700 for localizing inflammation of gingival tissue. In step 710, an inflammation localization system is provided. The inflammation localization system may be any of the devices or systems described or otherwise envisioned herein. Generally, the inflammation localization system will comprise one or more light emitters 42, one or more light detectors 40, and an inflammation detection and localization module 610 configured to analyze the data from the one or more light detectors. Many other components and configurations are possible. Although method 700 is described within the framework of an oral care device 10, the method can be implemented using any other inflammation localization analysis system or device.

At step 720 of the method, at least one light emitter 42 of the oral care device 10 emits light, a beam of which impacts the gingival tissue. According to an embodiment, the emitted light only indirectly impacts the gingival tissue that is analyzed by the light detector 40. The light emitted by the light emitter can be one or multiple wavelengths. Accordingly, the light emitter may comprise one or more light sources. The light emitter may emit light periodically or continuously, or may emit light only in response to a trigger.

For example, at optional step 715 of the method, the system detects tissue and activates light emitter 42 to emit light. The system may comprise a contact detection capability using a proximity signal such as an optical measurement using emitter/receiver architecture. Contact may be defined as the point where the signal detected by the receiver exceeds a pre-determined value, for example. This may help the system decipher between tissue and teeth when used in the mouth, for example. Many other methods of tissue detection and proximity detection are possible.

At step 730 of the method, at least one light detector 40 of the oral care device 10 obtains reflectance data, such as reflectance from the surfaces reflecting light emitted by the light emitter 42. The light detector may obtain a single data point or may obtain multiple data points over time. The light detector may obtain data periodically or continuously, or may only obtain data in response to a trigger. For example, the light detector may be triggered to obtain sensor data in response to activation of a light emitter.

As discussed herein, the light detector 40 is positioned in a non-overlapping position relative to the light emitter 42 such that the detected tissue is only indirectly illuminated by the light from the light emitter. This configuration of the light detector(s) and the light emitter(s) results in a significant improvement in both the device and detection of inflammation. For example, the non-overlapping configuration described or otherwise envisioned herein maximizes the signal-to-noise ratio and enhances detection of localized gingival inflammation, among other benefits, by reducing near-surface scattering and other inhibitory factors.

Figure 8:
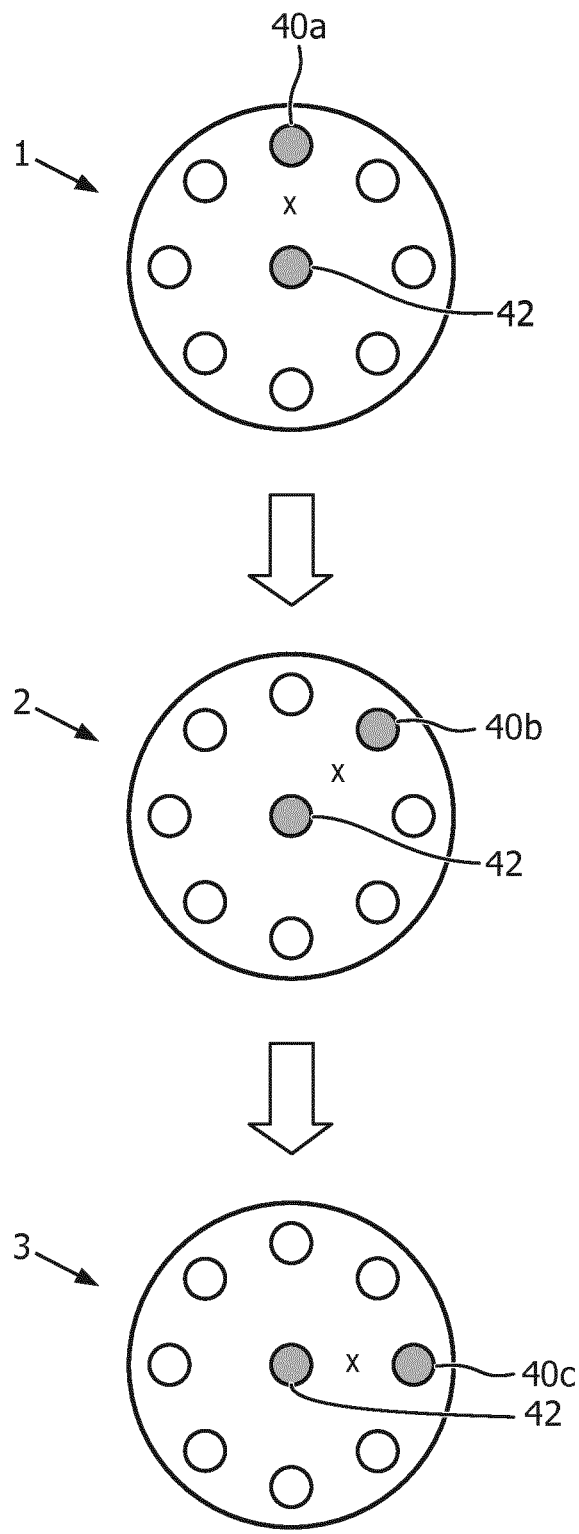
FIG. 8 is a series of schematic representations of a head of an oral care device, in accordance with an embodiment.

According to an embodiment, the light emitter and/or light detector are multiplexed. For example, as shown in the series in FIG. 8, the device comprises a single centralized light emitter 42 surrounded by a plurality of light detectors 40. In panel 1, the light emitter 42 is active and only one light detector, 40a, is obtaining reflectance data. The light detector obtains reflectance data from tissue that is approximately touching or near the "x" on the device. The light emitter may be on continuously in this series, or may emit light in sequence with the light detectors. In panel 2 of FIG.

8, the next light detector 40*b* is activated to obtain reflectance data from tissue that is approximately touching or near the "x" on the device. In panel 3 of FIG. 8, the next light detector 40*c* is activated to obtain reflectance data from tissue that is approximately touching or near the "x" on the device. This may continue until all light detectors obtain reflectance data, or until the user moves the device to a new location in the mouth, for example. Although the light detectors are shown obtaining reflectance data in sequence, any sequence or pattern may be used, including a completely randomized sequence or simultaneously, among others.

At optional step 740 of the method, a controller or processor of the oral care device analyzes the obtained reflectance data to determine which of the plurality of analyzed locations are and/or are not gingiva. For example, the light detectors 40 provide the obtained reflectance data to controller 30 where it is analyzed by processor 32 and/or inflammation detection and localization module 610, and/or stored in memory 34 for future analysis. This step may be performed continuously as the oral care device is utilized, may be performed in whole or in part after a cleaning session, and/or may be performed on demand.

According to one embodiment, the inflammation detection and localization module 610, which can be implemented as an algorithm, analyzes the obtained reflectance data in one or more steps. For example, as an initial step, the module rejects potential outliers in the data. Outliers may include spurious measurements, as well as reflectance data from objects that are likely not gingival tissues, such as food debris, teeth, and other objects. Since the absorption spectra of objects such as teeth and food debris vary considerably from the absorption spectra of gingival tissue, the two can be distinguished. According to an embodiment, outliers are detected at points with absorption spectra that do not correspond to gingival tissue, essentially not showing the sharp spectral characteristics of hemoglobin absorption.

Figure 9:
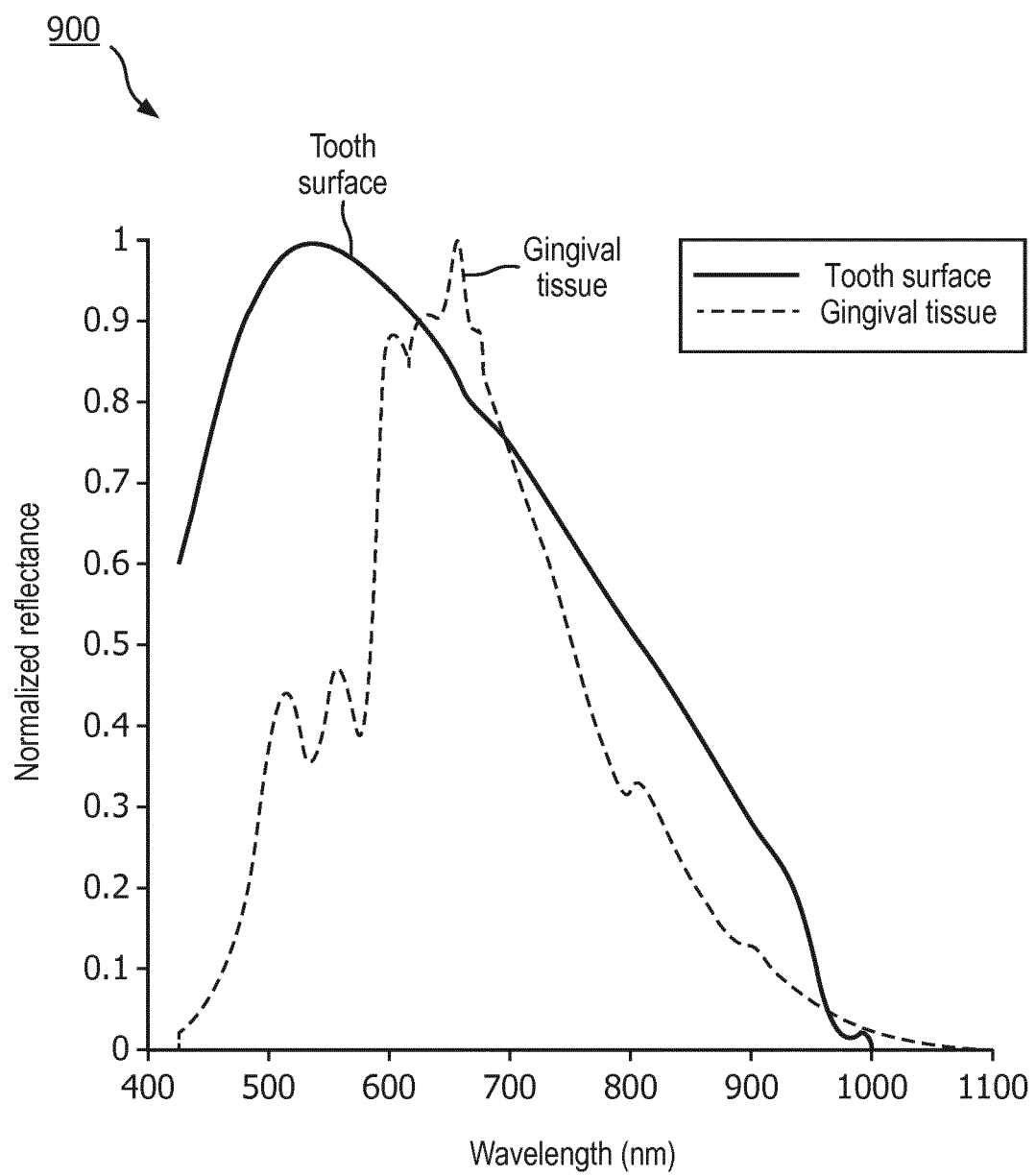
FIG. 9 is a graph of reflectance data, in accordance with an embodiment.

According to an embodiment, inflammation detection and localization module 610 determines a reflectance ratio of two different wavelengths. Using sample data of spectra obtained at 550 nm and 660 nm, for example, such as that shown in the spectral graph 900 in FIG. 9, a ratio of reflectance would provide values of 2.38 for gingival tissue and 1.21 for teeth. Similarly, a ratio of reflectance between a blue wavelength (400 nm to 480 nm) and a green wavelength (480 nm to 550 nm) would provide values of 5.96 for gingival tissue and 1.44 for teeth. Therefore, the inflammation detection and localization module 610 could be configured or programmed with predetermined thresholds to identify gingival tissue. According to an embodiment, the system compares the reflectance ratio to the predetermined threshold and characterizes the location as being gingiva or non-gingiva based on whether the determined reflectance ratio exceeds or does not exceed the predetermined threshold. As just one example, a threshold of 2 in both of the above examples would decipher between gingiva and non-gingiva; reflectance ratios above 2 are characterized as gingiva, and reflectance ratios below 2 are characterized as non-gingiva. The system would then discard data from non-gingiva and would only continue to analyze data obtained from gingiva.

According to another embodiment, at step 740 of the method the system analyzes the obtained reflectance data to determine which of the plurality of analyzed locations are and/or are not gingiva by weighting the reflectance data. For example, the system may apply a high weight to reflectance data indicative of gingiva, and/or may apply a low weight to reflectance data indicative of anything other than gingiva. A system configured to weight reflectance data may only apply a weight to reflectance data indicative of gingiva, may only apply a weight to reflectance data indicative of non-gingiva, or may apply weights to both conditions during an analysis. The weighting process may be a programmed or predetermined weighting process, or may be a machine-learned weighting process. Using a weighting process, the system may utilize the one or more weighting factors to focus on reflectance data indicative of gingiva for further analysis, including an analysis of possible inflammation.

In addition to removing non-gingiva reflectance data, and weighting gingiva and/or non-gingiva reflectance data, other methods of determining which of the plurality of analyzed locations are gingiva are possible.

At step 750 of the method, the inflammation detection and localization module 610 analyzes the reflectance data at one, some, or all locations obtained by the oral care device. This analysis can be done while the device is obtaining data, or may be completed after the oral care device has finished with a session, or it may be performed on demand from the user.

According to an embodiment, the inflammation detection and localization module 610 determines or characterizes an approximate tissue oxygenation level of the gingival tissue using the reflectance data. Since tissue oxygen saturation is significantly decreased in gingivitis and periodontitis locations compared to healthy locations, the module may select a signal exhibiting the lowest tissue oxygenation, which identifies the highest level of gingival inflammation. This may be performed, for example, by selecting the maximum value from a given set of data, or by taking the average of the X-top percentile from a given set of data, among other methods. The module may obtain this information, for example, at each locale for which data was obtained. The inflammation detection and localization module 610 will thus generate information about locations within the mouth where there is likely to be gingival inflammation.

At step 760 of the method, the system or device provides feedback to the user regarding the inflammation localization information. The user interface 46 of the oral care device 10, for example, can provide direct and/or indirect feedback to the user while the oral care device is being used, or after a cleaning or scanning session. As an example, the device can provide direct feedback to the user after each measurement using audio, visual, haptic, and/or digital feedback whenever inflammation is detected.

According to another embodiment, the system or device may provide feedback to the user after a scanning session is complete. As an example, the system or device may provide feedback once a scanning session is complete by means of visual representation where the inflammation levels are displayed. The feedback may include, for example, a mouth map—using location sensing technology during measurement—either in their absolute form to show the inflammation levels or in relative forms to highlight one or more specific sites. According to an embodiment, the device can scale or otherwise rank inflammation levels using a variety of colors or other physical representations. For example, the user may only focus on areas of significant inflammation, or inflammation above a certain level.

At optional step 770 of the method, the inflammation data is stored and/or communicated with a third party, either locally or remotely. For example, according to an embodiment, a patient may be instructed to use the oral care device during an appointment with a dental care professional, to assess inflammation. The inflammation information will then be communicated to the dental care professional, using a report or other mechanism. As another example, a user may collect inflammation data that is automatically or periodically transmitted to a remote healthcare professional or other intended or authorized entity where it can be analyzed continuously or during an appointment with the user.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The invention claimed is:

1. A method for localizing gingival inflammation within a user's mouth using an oral care device, the method comprising the steps of:
    identifying, by a first sensor, a plurality of positions and/or orientations of the oral care device within the user's mouth;
    emitting light by one or more light emitters of the oral care device;
    detecting, by one or more light detectors of the oral care device, reflectance from a surface at each of a plurality of locations corresponding to the sensed plurality of positions and/or orientations within the user's mouth to generate reflectance data for each of the plurality of locations, wherein the one or more light detectors each measure different parts of the surface at a location between the one or more light emitters and the one or more light detectors;
    determining, by a controller of the oral care device, which of the plurality of locations comprises gingiva;
    discarding reflectance data for locations determined not to comprise gingiva; wherein discarding reflectance data for locations determined not to comprise gingiva comprises generating a reflectance ratio for each of the plurality of locations, wherein the reflectance ratio comprises a measured value for a first wavelength of the reflectance data over a measured value for a second wavelength of the reflectance data; comparing the generated reflectance ratio to a predetermined threshold; and
    discarding reflectance data for each of the plurality of locations for which the generated reflectance ratio falls below the predetermined threshold; determining, by the controller, for each of the plurality of locations, whether gingiva at that location is inflamed; and
    providing, by user interface of the oral care device, information to the user regarding the inflamed location or locations.

2. The method of claim 1, wherein the one or more light emitters and the one or more light detectors are positioned such that the surface at each of the plurality of locations is not directly illuminated by the one or more light emitters.

3. The method of claim 1, wherein determining which of the plurality of locations comprise gingiva comprises weighting the generating reflectance data for at least some of the plurality of locations.

4. The method of claim 1, wherein the step of determining whether gingiva at one of the plurality of locations is inflamed comprises determining an approximate tissue oxygenation level of the gingiva at each of the remaining plurality of locations, wherein a low tissue oxygenation level indicates gingiva inflammation.

5. The method of claim 1, wherein the oral care device comprises a single light emitter and a plurality of light detectors.

6. The method of claim 1, wherein the oral care device comprises a single light detector and a plurality of light emitters.

7. A device configured to localize gingival inflammation within a user's mouth, the device comprising:
one or more sensors configured to sense a plurality of positions and/or orientations of the device within the user's mouth;
one or more light emitters configured to emit light when the device is at one or more of a plurality of locations corresponding to one or more of the sensed plurality of positions and/or orientations within the user's mouth;
one or more light detectors configured to generate reflectance data from a surface at each of the plurality of locations, wherein the one or more light detectors each measure different parts of the surface at a location between the one or more light emitters and the one or more light detectors;
a controller configured to determine, for each of the plurality of locations, whether that location comprises gingiva and to discard reflectance data for locations determined not to comprise gingiva; wherein the step of determining which of the plurality of locations comprise gingiva comprises: (i) generating a reflectance ratio for each of the plurality of locations, wherein the reflectance ratio comprises a measured value for a first wavelength of the reflectance data over a measured value for a second wavelength of the reflectance data; (ii) comparing the generated reflectance ratio to a predetermined threshold; and (iii) discarding reflectance data for each of the plurality of locations for which the generated reflectance ratio falls below the predetermined threshold; wherein the controller is further configured to determine, for each of the plurality of locations, whether gingiva at that location is inflamed; and
a user interface configured to provide information to the user regarding the inflamed location or locations.

8. The device of claim 7, wherein the one or more light emitters and the one or more light detectors are positioned such that the surface at each of the plurality of locations is not directly illuminated by the one or more light emitters.

9. An inflammation localization system configured to localize gingival inflammation within a user's mouth, the system comprising:
one or more light emitters each comprising one or more light sources configured to emit light within the user's mouth;
one or more light detectors configured to generate reflectance data from a surface at each of a plurality of locations within the user's mouth, wherein the one or more light detectors each measure different parts of the surface at a location between the one or more light emitters and the one or more light detectors;
one or more sensors configured to sense a plurality of positions and/or orientations corresponding to the plurality of locations within the user's mouth of the one or more light detectors;
a controller comprising an inflammation detection and localization module configured to determine, for each of the plurality of locations, whether that location comprises gingiva and to discard reflectance data for locations determined not to comprise gingiva; wherein discarding reflectance data for locations determined not to comprise gingiva comprises generating a reflectance ratio for each of the plurality of locations, wherein the reflectance ratio comprises a measured value for a first wavelength of the reflectance data over a measured value for a second wavelength of the reflectance data; comparing the generated reflectance ratio to a predetermined threshold; and
discarding reflectance data for each of the plurality of locations for which the generated reflectance ratio falls below the predetermined threshold; wherein the controller is further configured to determine whether gingiva at that location is inflamed; and
a user interface configured to provide information to the user regarding the inflamed location or locations.

10. The system of claim 9, wherein the one or more light emitters and the one or more light detectors are positioned such that the surface at each of the plurality of locations is not directly illuminated by the one or more light emitters.

11. The method of claim 1, wherein the one or more light detectors obtain reflectance data in a simultaneous sequence.

12. The device of claim 7, wherein the one or more light detectors obtain reflectance data in a simultaneous sequence.

13. The device of claim 7, wherein the device comprises a single light emitter and a plurality of light detectors.

14. The device of claim 7, wherein the device comprises a single light detector and a plurality of light emitters.

* * * * *